US010398377B2

(12) United States Patent
Amimori et al.

(10) Patent No.: US 10,398,377 B2
(45) Date of Patent: Sep. 3, 2019

(54) CONNECTOR SUBSTRATE, SENSOR SYSTEM, AND WEARABLE SENSOR SYSTEM (71) Applicant: JAPAN SCIENCE AND TECHNOLOGY AGENCY, Kawaguchi-shi (JP)

(72) Inventors: Ichiro Amimori, Tokyo (JP); Masao Nakajima, Tokyo (JP); Takao Someya, Tokyo (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

(21) Appl. No.: 15/756,410

(22) PCT Filed: Aug. 31, 2016

(86) PCT No.: PCT/JP2016/075406
§ 371 (c)(1),
(2) Date: Feb. 28, 2018

(87) PCT Pub. No.: WO2017/038849
PCT Pub. Date: Mar. 9, 2017

(65) Prior Publication Data
US 2018/0242912 A1    Aug. 30, 2018

(30) Foreign Application Priority Data

Sep. 4, 2015   (JP) .................................. 2015-174931

(51) Int. Cl.
A61B 5/06      (2006.01)
A61B 5/00      (2006.01)
(Continued)

(52) U.S. Cl.
CPC .......... *A61B 5/6804* (2013.01); *A61B 5/0024* (2013.01); *A61B 5/11* (2013.01);
(Continued)

(58) Field of Classification Search
CPC ................... H05K 2201/09227; A61B 5/6804
See application file for complete search history.

(56) References Cited

U.S. PATENT DOCUMENTS 3,750,094 A * 7/1973 Zenkich ............... A61B 5/0416
                                                 24/676
4,402,560 A * 9/1983 Swainbank ............ A61N 1/14
                                                 439/37
(Continued)

FOREIGN PATENT DOCUMENTS

JP    7-181511 A     7/1995
JP    11-513592 A   11/1999
(Continued)

OTHER PUBLICATIONS

International Search Report dated Oct. 11, 2016 in PCT/JP2016/075406 filed Aug. 31, 2016.

Primary Examiner — Ross N Gushi
(74) Attorney, Agent, or Firm — Oblon, McClelland, Maier & Neustadt, L.L.P.

(57) ABSTRACT

A connector substrate includes a base material, n first input terminals of m groups (m and n are an integer equal to or greater than 2) which are provided on the base material, n first output terminals which are provided on the base material, first wiring patterns which are disposed on or inside the base material and connect the first input terminals and the first output terminals, m second input terminals which are provided on the base material, m second output terminals which are provided on the base material, and second wiring patterns which are disposed on or inside the base material and connect the second input terminals and the second (Continued)

output terminals, in which a first end of each connector wiring constituting the first wiring pattern is connected to one of the n first input terminals constituting each group, and a second end is connected to one of the first output terminals.

10 Claims, 5 Drawing Sheets (51) Int. Cl.
| | |
|---|---|
| *H05K 1/18* | (2006.01) |
| *A61B 5/11* | (2006.01) |
| *H05K 1/03* | (2006.01) |
| *H05K 1/11* | (2006.01) |
| *H04Q 9/00* | (2006.01) |
| *A41D 1/00* | (2018.01) |

(52) U.S. Cl.
CPC ............. *H04Q 9/00* (2013.01); *H05K 1/038* (2013.01); *H05K 1/118* (2013.01); *H05K 1/18* (2013.01); *H05K 1/189* (2013.01); *A41D 1/005* (2013.01); *A61B 5/7267* (2013.01); *A61B 2562/046* (2013.01); *A61B 2562/164* (2013.01); *A61B 2562/166* (2013.01); *A61B 2562/222* (2013.01); *A61B 2562/227* (2013.01); *H05K 2201/09227* (2013.01); *H05K 2201/09445* (2013.01); *H05K 2201/10151* (2013.01)

(56) References Cited

U.S. PATENT DOCUMENTS

| | | | | | |
|---|---|---|---|---|---|
| 4,490,005 | A | * | 12/1984 | Hovey | A61B 5/0408 439/592 |
| 4,554,924 | A | * | 11/1985 | Engel | A61B 5/04087 252/500 |
| 4,617,935 | A | * | 10/1986 | Cartmell | A61B 5/04087 600/392 |
| 4,727,881 | A | * | 3/1988 | Craighead | A61B 5/04087 600/392 |
| 4,762,497 | A | * | 8/1988 | Burvee | H01R 4/64 439/179 |
| 5,003,673 | A | * | 4/1991 | Nysten | A44B 17/0005 24/662 |
| 5,115,548 | A | * | 5/1992 | Nysten | A44B 1/08 24/113 MP |
| 5,278,734 | A | * | 1/1994 | Ferber | A41D 27/085 362/103 |
| 5,406,945 | A | * | 4/1995 | Riazzi | A61B 5/0408 600/394 |
| 5,427,096 | A | * | 6/1995 | Bogusiewicz | A61B 5/0416 600/394 |
| 5,435,043 | A | * | 7/1995 | Ito | A41H 37/04 24/114.4 |
| 5,440,461 | A | * | 8/1995 | Nadel | A41D 27/085 362/103 |
| 5,458,141 | A | * | 10/1995 | Neil | A61B 5/0408 600/386 |
| 5,511,548 | A | * | 4/1996 | Riazzi | A61B 5/0408 600/391 |
| 5,645,063 | A | * | 7/1997 | Straka, Jr. | A61B 5/04085 600/391 |
| 5,798,907 | A | * | 8/1998 | Janik | G06F 1/163 361/679.03 |
| 5,855,818 | A | * | 1/1999 | Gan | A43B 7/36 252/503 |
| 6,170,129 | B1 | * | 1/2001 | Pferdehirt | A44B 17/0029 24/108 |
| 6,170,135 | B1 | * | 1/2001 | Pferdehirt | A44B 17/007 24/687 |
| 6,210,771 | B1 | * | 4/2001 | Post | H05K 3/10 428/100 |
| 6,315,009 | B1 | * | 11/2001 | Jayaraman | A41D 13/1281 139/387 R |
| 6,319,015 | B1 | * | 11/2001 | Faunce | H01R 11/22 24/662 |
| 6,324,053 | B1 | * | 11/2001 | Kamijo | G06F 1/163 2/264 |
| 6,474,830 | B1 | * | 11/2002 | Hansen | A44B 1/04 362/103 |
| 6,559,524 | B2 | * | 5/2003 | Seko | H01L 21/563 174/259 |
| 6,561,814 | B2 | * | 5/2003 | Tilbury | A41D 1/005 2/102 |
| 6,563,424 | B1 | * | 5/2003 | Kaario | G06F 1/163 340/572.1 |
| 6,617,521 | B1 | * | 9/2003 | Saito | H01L 24/27 174/260 |
| 6,745,082 | B2 | * | 6/2004 | Axelgaard | A61N 1/0472 600/372 |
| 6,800,001 | B1 | * | 10/2004 | Costa | H01R 11/22 439/859 |
| 6,854,988 | B2 | * | 2/2005 | Marmaropoulos | A41D 1/005 2/69 |
| 6,974,935 | B2 | * | 12/2005 | O'Grady | C08K 3/04 219/541 |
| 7,081,026 | B2 | * | 7/2006 | Schwarz | H01R 13/5224 439/729 |
| 7,144,830 | B2 | * | 12/2006 | Hill | D03D 1/0088 442/205 |
| 7,186,931 | B2 | * | 3/2007 | Chang | A44B 1/24 200/43.11 |
| 7,210,939 | B2 | * | 5/2007 | Marmaropoulos | A41D 1/005 2/69 |
| 7,245,957 | B2 | * | 7/2007 | Rowe | A61B 5/0408 600/391 |
| 7,336,499 | B2 | * | 2/2008 | Hagiwara | H01L 23/4985 174/254 |
| 7,611,255 | B1 | * | 11/2009 | Lagassey | A42B 1/244 362/103 |
| 8,123,576 | B2 | * | 2/2012 | Kim | A61B 5/0416 439/668 |
| 8,251,736 | B2 | * | 8/2012 | McIntire | A61B 5/0416 439/357 |
| 8,259,460 | B2 | * | 9/2012 | Bhattacharya | H05K 3/301 174/260 |
| 8,290,326 | B2 | * | 10/2012 | Furuyama | H05K 1/0274 385/129 |
| 8,357,858 | B2 | * | 1/2013 | Khosla | H01B 1/24 174/254 |
| 8,376,759 | B2 | * | 2/2013 | Debock | H01R 12/775 439/37 |
| 8,395,317 | B2 | * | 3/2013 | Bhattacharya | D03D 1/0088 313/491 |
| 8,406,843 | B2 | * | 3/2013 | Tiegs | A61B 5/0416 600/391 |
| 8,561,264 | B2 | * | 10/2013 | Hasegawa | A44B 17/0023 24/108 |
| 8,562,371 | B2 | * | 10/2013 | Biesse | H01R 4/4854 439/352 |
| 8,814,574 | B2 | * | 8/2014 | Selby | H01R 4/4854 439/37 |
| 8,975,004 | B2 | * | 3/2015 | Choi | C08F 2/44 252/500 |
| 9,032,762 | B2 | * | 5/2015 | Begriche | D04B 1/22 66/171 |
| 9,055,879 | B2 | * | 6/2015 | Selby | H01R 13/11 |
| 9,253,884 | B2 | * | 2/2016 | Jezewski | H05K 1/0393 |
| 9,282,893 | B2 | * | 3/2016 | Longinotti-Buitoni | A61B 5/6804 |
| 9,549,460 | B2 | * | 1/2017 | Watanabe | H05K 1/0216 |
| 9,795,027 | B2 | * | 10/2017 | Watanabe | H05K 1/025 |
| 2001/0036785 | A1 | * | 11/2001 | Takagi | D03D 15/00 442/229 |
| 2002/0076948 | A1 | * | 6/2002 | Farrell | B32B 3/08 438/800 |
| 2003/0211797 | A1 | * | 11/2003 | Hill | D03D 1/0088 442/205 |

(56) References Cited

U.S. PATENT DOCUMENTS

| | | | | |
|---|---|---|---|---|
| 2004/0004823 | A1* | 1/2004 | Sakata | H01L 23/4985 361/795 |
| 2004/0053518 | A1* | 3/2004 | Le Cloirec | H01R 4/04 439/37 |
| 2004/0173884 | A1* | 9/2004 | Kashiwagi | H05K 1/118 257/668 |
| 2004/0174663 | A1* | 9/2004 | Itokawa | H05K 1/147 361/600 |
| 2004/0244193 | A1* | 12/2004 | Jung | H05K 3/363 29/854 |
| 2005/0133249 | A1* | 6/2005 | Fujii | H05K 3/3452 174/250 |
| 2005/0205972 | A1* | 9/2005 | Sakata | H01L 23/4985 257/668 |
| 2006/0065956 | A1* | 3/2006 | Awata | H01L 23/49572 257/668 |
| 2006/0099849 | A1* | 5/2006 | Aeschbacher | H01R 12/78 439/495 |
| 2006/0124193 | A1* | 6/2006 | Orr | A61B 5/0002 139/421 |
| 2006/0213684 | A1* | 9/2006 | Sakata | H01L 23/49572 174/258 |
| 2010/0048066 | A1* | 2/2010 | Bertsch | H01R 4/58 439/696 |
| 2010/0100997 | A1* | 4/2010 | Lee | H01R 13/2407 2/69 |
| 2010/0202119 | A1* | 8/2010 | Nagami | H05K 1/0281 361/749 |
| 2012/0045168 | A1* | 2/2012 | Uemura | G02B 6/1221 385/14 |
| 2012/0236579 | A1* | 9/2012 | Uemura | H05K 1/0219 362/382 |
| 2013/0032381 | A1* | 2/2013 | Hiyama | H05K 1/028 174/254 |
| 2013/0133930 | A1* | 5/2013 | Watanabe | H05K 1/0281 174/254 |
| 2013/0214214 | A1* | 8/2013 | Carnahan | H01B 1/24 252/511 |
| 2014/0135960 | A1 | 5/2014 | Choi | |
| 2014/0370343 | A1* | 12/2014 | Nomoto | H01M 10/4207 429/90 |
| 2015/0136448 | A1* | 5/2015 | Sasaki | H05K 1/0281 174/251 |
| 2015/0357078 | A1* | 12/2015 | Lessing | G01L 1/20 73/774 |
| 2018/0124916 | A1* | 5/2018 | Hattori | H01L 23/498 |
| 2018/0140901 | A1* | 5/2018 | Wiebe | A63B 24/0075 |
| 2018/0271441 | A1* | 9/2018 | Dabby | D03D 1/0088 |

FOREIGN PATENT DOCUMENTS

| | | |
|---|---|---|
| JP | 2012-214968 A | 11/2012 |
| JP | 2014-25180 A | 2/2014 |
| JP | 5535950 B2 | 7/2014 |
| WO | WO 97/14358 A1 | 4/1997 |
| WO | WO 2009/114689 A1 | 9/2009 |
| WO | WO 2014/155888 A1 | 10/2014 |

\* cited by examiner

CONNECTOR SUBSTRATE, SENSOR SYSTEM, AND WEARABLE SENSOR SYSTEM

TECHNICAL FIELD

The present invention relates to a connector substrate, a sensor system, and a wearable sensor system.

Priority is claimed on Japanese Patent Application No. 2015-174931, filed on Sep. 4, 2015, the content of which is incorporated herein by reference.

BACKGROUND ART

In recent years, flexible electronics has various application uses because of softness of their materials and thus has attracted much attention. For example, the flexible electronics has gained attraction as a means for directly obtaining biological information such as the movement of a human body by wearing on the surface of the human body or in the body.

For example, Patent Document 1 discloses clothing provided with a sensor that performs follow-up management of the performance of an individual who is performing motion activity. For example, Patent Document 2 discloses clothing in which a wiring portion is provided integrally with a fabric body. It is disclosed that it is possible to suppress the breaking of the wiring portion and the obstruction of a wearer's action by providing the wiring portion integrally with the fabric body.

Patent Document 3 discloses a sensor in which a plurality of measurement points are disposed in a regular array in order to also obtain planar positional information.

Patent Document 4 discloses clothing in which a plurality of motion sensors, such as acceleration sensors, are disposed over the whole body.

Signals acquired by the sensors are output to the outside and measured. For example, Patent Document 5 discloses that an electrode attached to a subject and a monitoring device are connected to each other by a connector and are output to the outside. Patent Document 1 discloses that physiological data is transmitted and received using a transceiver connected to the sensor, and Patent Document 2 discloses that information is wirelessly transmitted to the outside by using a transmission module connected to the sensor. Patent Document 4 discloses a system which is connected to communication means through a controller.

CITATION LIST

Patent Literature

[Patent Document 1] Japanese Unexamined Patent Application, First Publication No. 2012-214968
[Patent Document 2] Japanese Unexamined Patent Application, First Publication No. 2014-25180
[Patent Document 3] Japanese Patent No. 5535950
[Patent Document 4] United States Patent Application, Publication No. 2014/0135960
[Patent Document 5] Published Japanese Translation No. H11-513592 of the PCT International Publication

SUMMARY OF INVENTION

Technical Problem

The inventors have examined a sensor system capable of measuring the movement of a human body, and have noticed that there are various problems. There have been demands for a sensor system capable of solving such various problems at once.

One of the problems noticed by the inventors is that a sensor system which is capable of aggregately measuring not only information from a specific position but also information from various positions and has a good feeling of wearing has not been realized.

For example, in Patent Document 1 and Patent Document 2, the sensor is provided at a predetermined position in a human body, and only information on the portion is measured. For this reason, for example, it is difficult to obtain a plurality of pieces of information on the human body's arm, leg, trunk, and the like at once.

In order to obtain the plurality of pieces of information at once, the sensors as disclosed in Patent Document 1 and Patent Document 2 can be simultaneously attached at various positions of the human body. However, it is not realistic to attach the plurality of sensors at once. In order to simultaneously output pieces of information obtained from the sensors to the outside, one transceiver or transmission module is necessary for each sensor, and thus the sensor system becomes extremely large. In Patent Document 4, a plurality of pieces of information are aggregately measured by the controller. However, in order to perform communication by connection of a plurality of acceleration sensors, a wiring or the controller necessarily becomes extremely large.

The large-scale sensor system also results in a problem that the sensor system gives a sense of incongruity to a wearer. For example, in a case where measurement is performed throughout the whole day, or the like, the badness of a feeling of wearing of the sensor system gives an extremely large burden on the wearer. In such a sensor system that causes a sense of incongruity for a wearer, information based on daily life is hardly obtained.

It is also considered that one external output means such as a transceiver or a transmission module is provided, and pieces of information are collectively transmitted to one external output means. However, as a result of the inventor's examination, the inventors have noticed that it is necessary to electrically connect each of the sensors and the external output means to each other in order to integrate information to one external output means, which results in another problem.

In order to electrically connect each sensor and one external output means to each other, connection points corresponding to a number, which is obtained by adding a ground wire to the number of wirings from the sensors, are at least required, and a connector having the connection points is required (for example, FIGS. 3 and 4 in Patent Document 5). As the number of sensors increases, the number of connection points increases.

In a connector having a large number of connection points, it is necessary to separately dispose the connection points, which results in an increase in size of the connector. In a wearable sensor system, such a large connector causes a sense of incongruity during the wearing of the wearable sensor system. In a case where the sensor system is used for clothing and the like, cloth is pulled by the connector, and thus there is a concern that accurate measurement is hindered.

In a connector having a large number of connection points, there is a possibility that terminals to be connected to each other are mistaken. Further, it takes time to perform both an operation of reliably performing connection of all of the connection points and an operation of confirming the reliable connection of the connection points. That is, it is not possible to easily and simply connect each sensor and the external output means to each other.

The inventors have also noticed that another problem occurs due to an increase in number of connection points of a connector. The problem is that it is difficult to wash clothing and the like in a case where a sensor system is provided in the clothing and the like. Either of wireless type external output means or wired type external output means is required to be removed during washing. However, when the number of connection points of a connector is increased, it is difficult to simply remove the external output means.

In addition, the connector provided on the clothing side is washed together with the clothing during the washing. When the connector increases in size, it is assumed that large stress is applied to the connector during the washing. As a result, there is a strong possibility that the connector is peeled off from the clothing or is broken.

On the other hand, in principle, it is possible to reduce the number of connection points by converting an input signal into a matrix at a stage prior to arrival at the connection point and integrating signals (for example, Patent Document 3 and the like). However, pieces of information from sensor points, which are regularly disposed in a matrix, are electrically processed inside a sensor. In other words, when the sensor points are not regularly disposed, it is not possible to convert the signals into a matrix inside the sensor. That is, it is not possible to integrate the signals from the sensor points that are irregularly disposed. For this reason, this is not usable in a case where pieces of information from various points of a human body or the like are integrated, and thus the degree of freedom as a sensor system is low.

The invention is contrived in view of such situations, and an object thereof is to realize a sensor system which is capable of solving the above-described problems at once. More specifically, an object thereof is to provide a connector substrate which is capable of suppressing a wearer's sense of incongruity during the wearing of the sensor system and facilitating attachment and detachment of external output means. In addition, an object thereof is to provide a sensor system which is capable of measuring pieces of information from sensors at once and suppressing a wearer's sense of incongruity and which is washable.

Solution to Problem

The inventors have found a connector substrate in which signals from sensors are physically classified by a wiring pattern and the number of output terminals can be reduced, as a result of wholehearted examination. In addition, the inventors have found that when the connector substrate is used, a wearer's sense of incongruity is suppressed when wearing a sensor system, and attachment and detachment of external output means are facilitated, and have completed the invention.

That is, in order to solve the above-described problems, the invention has adopted the following means.

(1) According to an aspect of the invention, there is provided a connector substrate including a base material, n first input terminals of m groups (m and n are an integer equal to or greater than 2) which are provided on the base material, n first output terminals which are provided on the base material, first wiring patterns which are disposed on or inside the base material and connect the first input terminals and the first output terminals, m second input terminals which are provided on the base material, m second output terminals which are provided on the base material, and second wiring patterns which are disposed on or inside the base material and connect the second input terminals and the second output terminals, in which a first end of each connector wiring constituting the first wiring pattern is connected to one of the n first input terminals constituting each group, and a second end is connected to one of the first output terminals.

(2) In the connector substrate according to (1), the base material may be flexible.

(3) In the connector substrate according to (1) or (2), the first input terminals and the second input terminals may be provided in an outer peripheral portion of the base material, the first output terminals and the second output terminals may be provided in a center portion of the base material, and the first wiring patterns and the second wiring patterns may be present at different positions in a thickness direction of the base material inside the base material or on an outer surface of the base material.

(4) According to another aspect of the invention, there is provided a sensor system including the connector substrate according to any one of (1) to (3), a plurality of sensors which are classified into m groups, a first wiring which connects each of the plurality of sensors and the first input terminals of the connector substrate to each other, a second wiring which connects the sensors constituting one group, among the plurality of sensors, and is connected to the second input terminals of the connector substrate, external output means, connected to the connector substrate, for outputting a signal to the outside, and signal processing means which is configured to process the signal which is output by the external output means.

(5) In the sensor system according to (4), the plurality of sensors may be irregularly disposed.

(6) In the sensor system according to (4) or (5), the first wiring and the second wiring may not intersect each other when seen in a plan view until reaching the connector substrate from each of the plurality of sensors.

(7) In the sensor system according to any one of (4) to (6), the connector substrate and the external output means may be connected to each other by a magnet.

(8) In the sensor system according to any one of (4) to (7), the signal processing means may perform machine learning.

(9) In the sensor system according to any one of (4) to (8), the plurality of sensors may cause a change in resistance due to a change in at least one physical quantity selected from a group consisting of sound, light, temperature, pressure, and distortion.

(10) According to still another aspect of the invention, there is provided a wearable sensor system including a fabric body to which the plurality of sensors and the connector substrate in the sensor system according to any one of (4) to (9) are attached, in which the first wiring and the second wiring are provided integrally with the fabric body.

Advantageous Effects of Invention

A connector substrate according to an aspect of the invention suppresses a wearer's sense of incongruity during the wearing of a sensor system, and facilitates attachment and detachment of external output means.

A sensor system according to another aspect of the invention can measure pieces of information from sensors, which are irregularly disposed, at once and can limit a wearer's sense of incongruity, and is washable.

DESCRIPTION OF EMBODIMENTS

Hereinafter, configurations of a connector substrate, a sensor system, and a wearable sensor system according to this embodiment will be described with reference to the accompanying drawings. In the drawings used in the following description, characteristic portions may be enlarged in order to facilitate the understanding of the characteristics for convenience, and the dimensional ratio of each component is not necessarily the same as the actual dimensional ratio. Materials, dimensions, and the like illustrated in the following description are merely examples, and the invention is not limited thereto. The materials, dimensions, and the like can be appropriately changed without departing from the scope of the invention.

(Sensor System)

Figure 1:
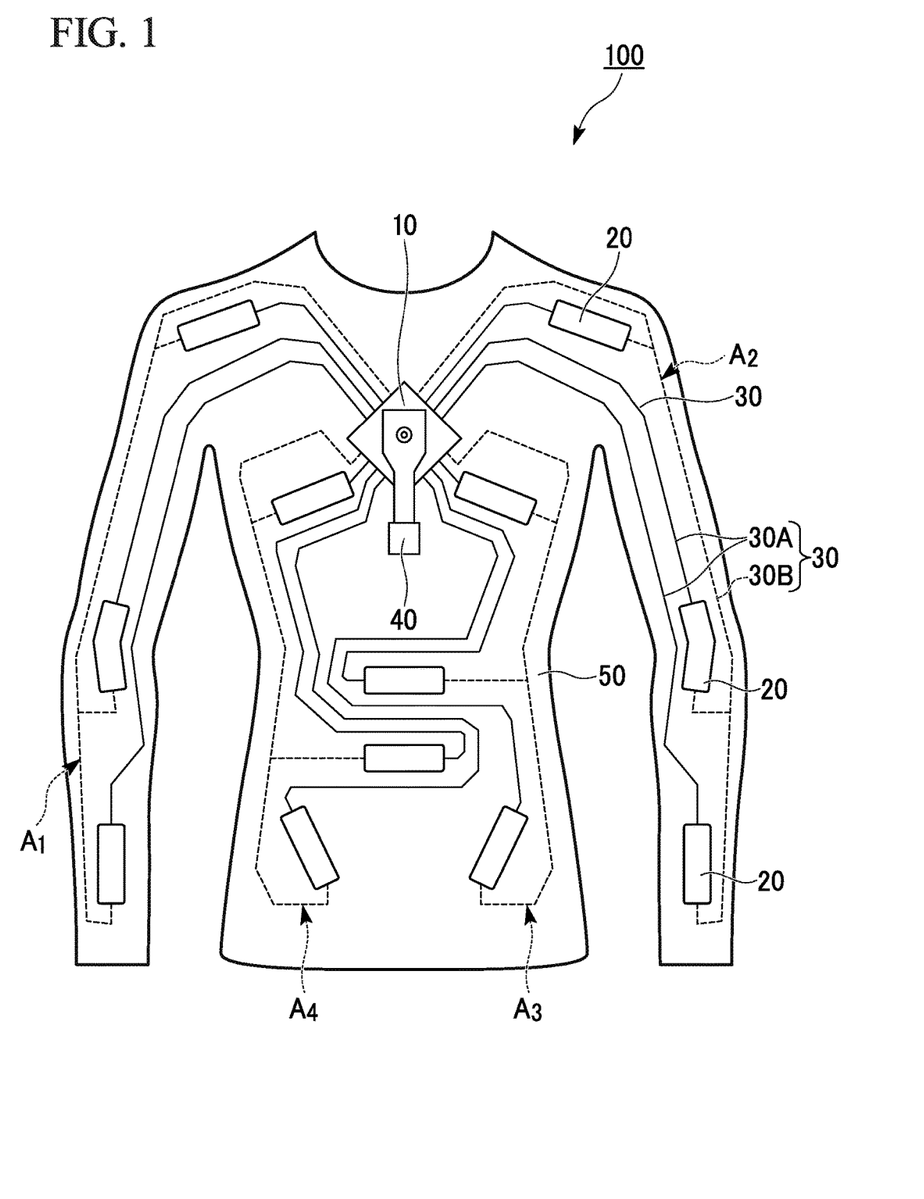
FIG. 1 is a schematic diagram of a sensor system according to an aspect of the invention.

FIG. 1 is a schematic diagram of a sensor system according to an aspect of the invention.

A sensor system 100 shown in FIG. 1 includes a connector substrate 10, a plurality of sensors 20, a plurality of wirings 30, external output means 40, and signal processing means (not shown). The plurality of wirings 30 connect the sensor 20 and the connector substrate 10 to each other. The external output means 40 is connected to the connector substrate 10. The signal processing means processes a signal which is output from the external output means 40.

The sensor system 100 shown in FIG. 1 is a wearable clothing type sensor system in which the sensor 20 is attached to a fabric body 50 and the wirings 30 are provided integrally with the fabric body 50. The sensor system according to the aspect of the invention is not limited to the configuration shown in FIG. 1. For example, the fabric body 50 and the sensor system can be separated from each other. In addition, the sensor system is not limited to a clothing type that covers the whole body as shown in FIG. 1, and may be configured to cover only a portion of the body. In addition, the sensor system may be configured to be worn by an animal in order to confirm an action of an animal, such as a dog, or a robot.

In a case of the wearable clothing type sensor system 100 shown in FIG. 1, a method of attaching the fabric body 50, the connector substrate 10, and the sensor 20 is not particularly limited. For example, the connector substrate 10 and the sensor 20 may be bonded to the fabric body 50 by using an adhesive or the like, or the connector substrate 10 and the sensor 20 may be woven into the fabric body 50. In addition, regarding the sensor 20, a sensor formed using ink may be printed on the fabric body 50.

When the fabric body 50 and the sensor system 100 are integrally formed, it is possible to reduce a sense of incongruity during the wearing of the sensor system 100. The followability of the sensor system 100 with respect to the fabric body 50 increases. As a result, it is possible to perform more accurate measurement. Stress when stretching a fabric body with a sensor by 50% is in a range between one twentieth and 20 times when stretching only the fabric body, preferably between one tenth and 10 times, and more preferably between one fifth and 5 times.

The plurality of sensors 20 are classified into m groups $A_1$ to $A_m$ for each region. In FIG. 1, the sensors are classified into four groups $A_1$ to $A_4$. Each of the groups $A_1$ to $A_4$ includes n sensors. In FIG. 1, each of m=4 groups includes n=3 sensors 20. The number of groups and the number of sensors are not limited to this case, and can vary depending on the mode of use.

The wiring 30 includes a first wiring 30A and a second wiring 30B. The first wiring 30A connects each of the sensors 20 and the connector substrate 10 to each other. The second wiring 30B connects the sensors 20 constituting one group, and is connected to the connector substrate 10. That is, each sensor is connected to each of the first wiring 30A and the second wiring 30B.

In FIG. 1, for example, three sensors 20 included in the right arm group $A_1$ are connected to the connector substrate 10 by the first wiring 30A. In addition, three sensors 20 included in the right arm group $A_1$ are connected to each other by the second wiring 30B, and integrated into one wiring to be connected to the connector substrate 10. That is, from the right arm group $A_1$, the number (four) of wirings 30 obtained by adding one wiring to the number (three) of sensors included in the right arm group $A_1$ are connected to the multi-point sensor connector substrate 10. This is not limited to the right arm group $A_1$, and is the same as in the left arm group $A_2$, the left trunk group $A_3$, and the right trunk group $A_4$. As a result, on the connector substrate 10, a total of 16 wirings 30 including four wirings (three first wirings 30A+one second wiring 30B) by four groups are disposed.

When generalizing this, a total of m second wirings 30B respectively obtained from the m groups $A_1$ to $A_m$ are connected to the connector substrate 10. In addition, the first wirings 30A respectively obtained from all of the sensors 20 included in each of the groups $A_1$ to $A_m$ are connected thereto. For convenience of description, when the number of sensors included in each of the groups $A_1$ to $A_m$ is set to be n, m×n first wirings 30A are connected thereto. That is, the number of wirings 30 connected to the connector substrate 10 is m×n+m=m×(n+1) in total.

<Connector Substrate>

Figure 2:
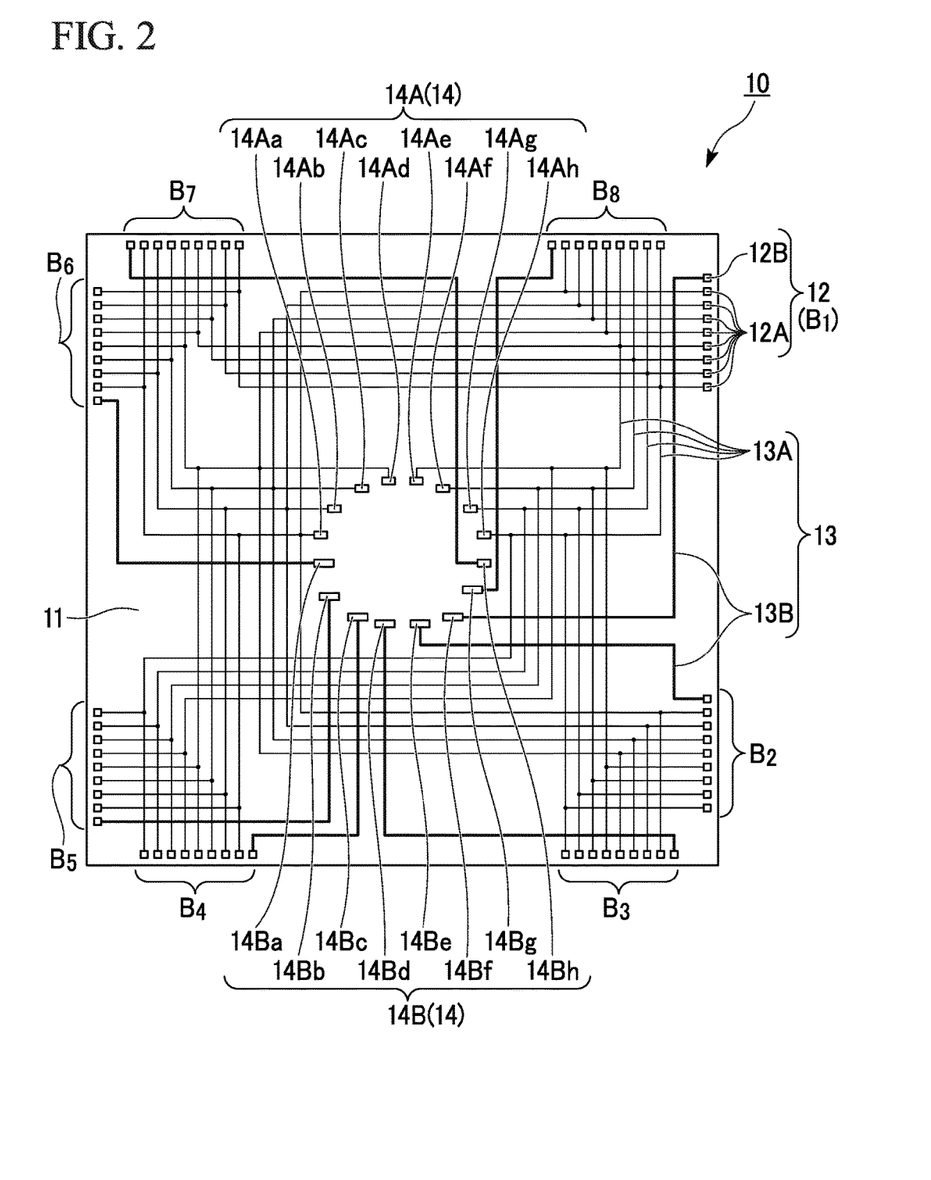
FIG. 2 is a schematic diagram showing a connector substrate according to the aspect of the invention when seen in a plan view.

FIG. 2 is a schematic diagram showing a connector substrate according to the aspect of the invention when seen in a plan view.

The connector substrate 10 shown in FIG. 2 includes a base material 11, first input terminals 12A, second input terminals 12B, first wiring patterns 13A, second wiring patterns 13B, a first output terminal 14A, and a second output terminal 14B. Hereinafter, the first input terminal 12A and the second input terminal 12B may be collectively referred to as an external input terminal 12, the first wiring pattern 13A and the second wiring pattern 13B may be collectively referred to as a wiring pattern 13, and the first output terminal 14A and the second output terminal 14B may be collectively referred to as an external output terminal 14.

The base material 11 has an insulating property, and supports the external input terminal 12, the internal wiring pattern 13, and the external output terminal 14. The base material 11 is preferably a flexible material. Here, the term "flexible" means being capable of being freely bent to a degree of a flexible printed circuit (FPC). The base material 11 has flexibility, and thus is hardly damaged even when stress is applied to the connector substrate 10 due to processing such as washing.

Examples of a material used for the base material 11 may include polyimide (PI), polyethylene terephthalate (PET), and the like.

The external input terminal 12 is an electrical contact point formed on the base material 11. The external input terminal 12 includes the first input terminal 12A and the second input terminal 12B. Each of the first input terminal 12A and the second input terminal 12B may be disposed on the same surface as that of the base material 11, or may be disposed on a surface different from that of the base material. The first input terminal 12 can be connected to each of the plurality of sensors 20. The second input terminal 12B can be connected to the sensors 20 included in one group. That is, the connector substrate 10 functions as a connector substrate for multi-point sensor which is capable of being connected to a multi-point sensor.

In the external input terminal 12 of FIG. 2, six first input terminals 12A and one second input terminal 12B constitute one group, and thus a total of eight groups are provided. The groups $B_1$ to $B_m$ respectively correspond to the groups $A_1$ to $A_m$ into which the plurality of sensors 20 in the sensor system 100 are divided for each region.

For example, the group $B_1$ in FIG. 2 can be connected to the right arm group $A_1$ in FIG. 1. That is, although only three sensors 20 are shown in FIG. 1 for convenience of illustration, each of six sensors disposed in the right arm group $A_1$ can be connected to the first input terminal 12A through the first wiring 30A. In addition, the second input terminal 12B can be connected to each sensor 20 disposed in the right arm group $A_1$ through the second wiring 30B. Similarly, each of the left arm group $A_2$, the left trunk group $A_3$, and the right trunk group $A_4$ in FIG. 1 can be connected to each of the groups $B_2$ to $B_4$ in FIG. 2.

In FIG. 2, the external input terminal 12 includes eight groups $B_1$ to $B_8$. For this reason, in a case where the connector substrate 10 of FIG. 2 is used, four groups $A_5$ to $A_8$ can also be further provided in the sensor system 100 of FIG. 1.

The number of groups of the groups $B_1$ to $B_m$ can appropriately vary depending on the number of groups $A_1$ to $A_m$ provided in the sensor system 100. In addition, the number of first input terminals 12A constituting the groups $B_1$ to $B_m$ can also vary depending on the number of sensors included in each of the groups $A_1$ to $A_m$.

The external output terminal 14 is an electrical contact point formed on the base material 11. The external output terminal 14 includes the first output terminal 14A and the second output terminal 14B. The first output terminal 14A and the second output terminal 14B may be disposed on the same surface as that of the base material 11, or may be disposed on a surface different from that of the base material. The number of terminals of the first output terminal 14A corresponds to the maximum number of the first input terminal 12A in the groups $B_1$ to $B_m$. On the other hand, the number of terminals of the second output terminal 14B corresponds to the number of groups of the groups $B_1$ to $B_m$.

The external input terminal 12 and the external output terminal 14 may be formed of a conductive material, and can be manufactured using, for example, solder, silver paste, copper, or the like.

The wiring pattern 13 is disposed on or inside the base material 11. The wiring pattern 13 includes the first wiring pattern 13A and the second wiring pattern 13B. The first wiring pattern 13A connects the input terminal 12A and the output terminal 14A to each other. The second wiring pattern 13B connects the second input terminal 12B and the second output terminal 14B to each other.

Each connector wiring constituting the wiring pattern 13A connects the first input terminal 12A and the first output terminal 14A. A first end of each connector wiring constituting the wiring pattern 13A is connected one of the n first input terminals 12A constituting the groups $B_1$ to $B_m$. On the other hand, a second end of each connector wiring constituting the wiring pattern 13A is connected one of the first output terminals 14A. That is, each connector wiring constituting the wiring pattern 13A extends from one of the n first input terminals 12A of each group, and the connector wirings are disposed so as to be integrated into one until reaching the first input terminal 14A.

For example, in FIG. 2, the connector wirings extending to the first output terminal 14A from one of the first input terminals 12A constituting one group $B_1$ are connected to the connector wirings extending from one of the first input terminals 12A constituting each of the other groups $B_2$ to $B_8$, until reaching the first output terminal 14A. That is, a total of 64 input terminals 12A are integrated into eight output terminals 14A.

On the other hand, the second wiring pattern 13B connects the second input terminal 12B and the second output terminal 14B. Connector wirings constituting the second wiring pattern 13B are not connected to the connector wirings constituting the first wiring pattern 13A and the other connector wirings constituting the second wiring pattern.

A configuration of the connector substrate 10 has been described above. Subsequently, functions of the connector substrate 10 will be described.

The connector substrate 10 converts pieces of information which are input from m×(n+1) external input terminals 12 by matrix scanning, and output the information by m+n external output terminals 14.

The conversion by the matrix scanning is performed in the following sequence. For example, when a subject wearing the sensor system 100 moves the right arm, any one sensor 20 in the right arm group $A_1$ in FIG. 1 responds. In this case, a number is virtually given to sensors included in the right arm group $A_1$. For example, it is assumed that the sensor 20 of number 2 in the right arm group $A_1$ responds.

Information indicating that the sensor 20 of number 2 in the right arm group $A_1$ responds is transmitted to the connector substrate 10 by the first wiring 30A and the second wiring 30B. In this case, the first wiring 30A is directly connected to the connector substrate 10, the information indicating that the sensor 20 of number 2 in the right arm group $A_1$ responds is transmitted as it is. On the other hand, the second wiring 30B is also connected to the other sensors 20 in the right arm group $A_1$, and thus information indicating that any one sensor in the right arm group $A_1$ responds is transmitted.

The information transmitted from the first wiring 30A is input to, for example, the first input terminal 12A, which is the second terminal from the top in the drawing, in the group $B_1$ of the connector substrate 10 shown in FIG. 2. The input information is transmitted to the first output terminal 14A through the first wiring pattern 30A. Here, connector wirings constituting the first wiring pattern 30A is also connected to the first input terminal 12A, which is the second terminal, in the other groups. That is, the information, indicating that the sensor 20 of number 2 in the right arm group $A_1$ responds, which is transmitted to the first input terminal 12A is replaced by information indicating that the second sensor 20 in any one of the groups $A_1$ to $A_n$ responds, at a stage where the information reaches the first output terminal 14A.

On the other hand, the information transmitted from the second wiring 30B is input to, for example, the second input terminal 12B in the group $B_1$ of the connector substrate 10 shown in FIG. 2. The information which is input to the second input terminal 12B is transmitted to the second output terminal 14B as it is through the second wiring pattern 13B. That is, information indicating that any one sensor in the right arm group $A_1$ responds is transmitted to the second output terminal 14B as it is.

As a result, in signal processing means to be described later, information, indicating that a predetermined sensor in any one group, which is output from the first output terminal 14A is compared with information, indicating that any one sensor in a predetermined group, which is output from the second output terminal 14B, and thus it is possible to read that a predetermined sensor in a predetermined group responds. In this case, the comparison between the pieces of information can be determined by comparing potential differences of the first output terminal 14A and the second output terminal 14B with each other.

Figure 3:
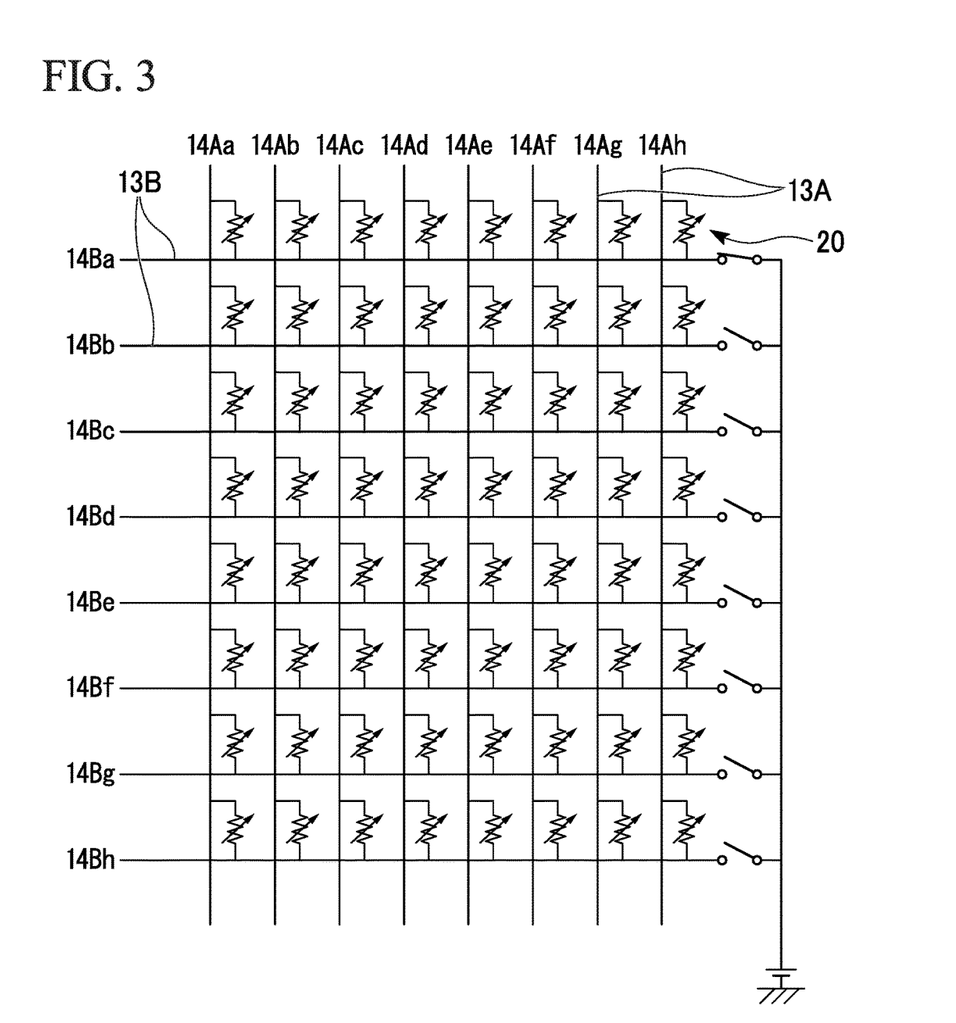
FIG. 3 is a schematic circuit diagram showing a matrix scanning circuit which is virtually formed in the sensor system according to the aspect of the invention.

FIG. 3 is a schematic circuit diagram showing a matrix scanning circuit which is virtually formed in the sensor system according to the aspect of the invention. A variable resistor in FIG. 3 corresponds to each sensor 20 in FIG. 1. Terminals 14Aa to 14Ah and 14Ba to 14Bh in FIG. 2 correspond to ends in row and column directions in FIG. 3.

In FIG. 3, when any one sensor 20 responds, a resistance value of the variable resistor changes. Information indicating the change in the resistance value is also transmitted in any of the row and column directions. In this case, information transmitted in the column direction is information, indicating that a predetermined sensor in any one group responds, which is converted by the first wiring pattern 30A in the above description. On the other hand, information transmitted in the row direction is information, indicating that any one sensor in a predetermined group responds, which is converted by the second wiring 30B.

Here, regarding voltage measurement by a passive matrix circuit as shown in FIG. 3, the generation of a current in an OFF line which is referred to as a sneak current may become a problem. However, as a solution therefor, for example, Takahashi, Y et al., 2005 IEEE/RSJ Int. Conf. Intell. Robot. Syst. IROS 1097-1102 (2005) is known.

As described above, the wiring 30 in the sensor system 100 and the wiring pattern 13 in the connector substrate 10 virtually perform matrix conversion of information. For this reason, in the connector substrate 10, it is possible to reduce m×(n+1) external input terminals to m+n external output terminals.

Specifically, in FIG. 2, signals from a total of 64 sensors of the first input terminal 12A and the second input terminal 12B can be output by a total of 16 output terminals of the first output terminal 14A and the second output terminal 14B. Normally, a total 65 external output terminals obtained by adding up 64 sensors and an earth are required, while the number of external output terminals is drastically reduced to 16 by using the connector substrate 10 according to the aspect of the invention. The principle of the conversion is the same as a principle used when the number of external output terminals is reduced using matrix conversion in which information from sensors disposed on a matrix based on a CCD or the like is read out by wirings disposed in a matrix.

Here, it is preferable that the sensors 20 are irregularly disposed. The phrase "irregularly disposed" means that the sensors are not disposed in a matrix. For example, with respect to the connector substrate 10, a case where the sensors are provided at a plurality of locations at equal distances does not correspond to "regular disposition" in this specification.

In principle, a reduction in the number of output signals by conversion of input signals into a matrix has also been performed in the related art (for example, Patent Document 3 and the like). However, this is used when signals from sensors regularly disposed in a matrix are processed, and is not applicable to the processing of signals from sensors irregularly disposed. In the connector substrate 10 according to the aspect of the invention, even signals from the sensors 20 irregularly disposed can be arranged again in a virtual matrix by converting the signals into a matrix of m rows by n columns by the wiring pattern 13. That is, unlike matrix scanning being regularly performed on signals regularly disposed, signals irregularly disposed are virtually and regularly disposed and matrix scanning is performed thereon. The phrase "signals from sensors irregularly disposed are arranged again in a virtual matrix" is not conceivable from sensors regularly arranged.

The application of such a function to the connector substrate 10 is conceivable only by the inventors who have found that it is necessary to reduce the number of connection points of the connector substrate 10 in order to solve a problem that it is necessary to facilitate attachment and detachment and to realize a washable sensor system.

In the connector substrate 10, it is preferable that the external input terminal 12, the internal wiring pattern 13, and the external output terminal 14 are disposed as shown in FIG. 2. That is, it is preferable that the first input terminals 12A and the second input terminal 12B included in the external input terminal 12 are disposed in the outer peripheral portion of the base material 11, and the first output terminals 14A and the second output terminals 14B included in the external output terminal 14 are disposed in the center portion of the base material 11. The number of terminals of the external input terminal 12 is larger than the number of terminals of the external output terminal 14. For this reason, the external input terminal 12 is disposed in the outer peripheral portion having a large area allowable for disposition, and the internal wiring pattern 13 is disposed so as to converge toward the external output terminal 14 in the center position, so that it is possible to efficiently use the base material 11 and to reduce the size of the connector substrate 10.

It is preferable that the first wiring pattern 13A and the second wiring pattern 13B are disposed at positions of different depths in the thickness direction of the base material 11. For example, the first wiring pattern 13A can be disposed on one surface of the base material 11, and the second wiring pattern 13B can be disposed on a surface opposite to the surface.

The first wiring pattern 13A and the second wiring pattern 13B are disposed at positions of different depths in the thickness direction of the base material 11, and thus it is possible to prevent the wiring patterns from being electrically connected to each other. When the first wiring pattern 13A and the second wiring pattern 13B are electrically connected to each other, it is not possible to appropriately read out the sensor 20 which is driven. In addition, the connector wirings constituting the first wiring pattern 13A can also be disposed at positions of different depths in the thickness direction of a base material so as not to be electrically connected to each other.

The wiring pattern 13 can be formed on the base material 11 by patterning. The wiring pattern 13 may be formed using a mask having a predetermined opening by deposition, sputtering, or the like, or may be formed by wet etching or dry etching after a metal film is formed. In a case where the base material 11 has a laminated structure, the base material 11 having the first wiring pattern 13A formed thereon and the base material having the second wiring pattern 13B formed thereon may be bonded to each other by processing, such as heating, so that the respective connector wirings thereof are not electrically connected to each other.

<External Output Means>

Figure 4:
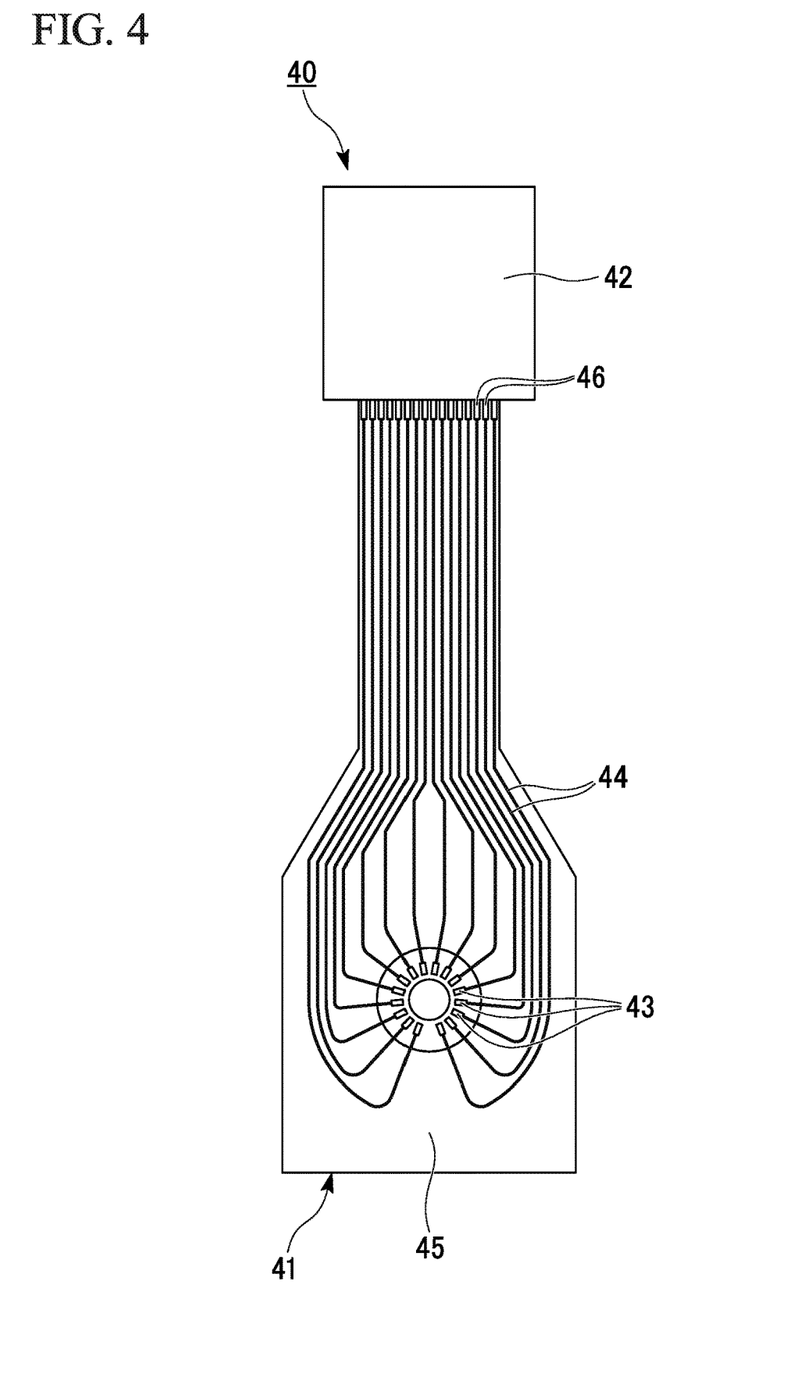
FIG. 4 is an example of a schematic plan view showing external output means.

The external output means 40 is connected to the connector substrate 10. The external output means 40 includes a connector portion 41 connected to the connector substrate 10 and a signal transmission unit 42 that outputs an input signal to the outside through the connector portion 41. FIG. 4 is an example of a schematic perspective view showing the external output means.

The connector portion 41 shown in FIG. 4 includes a plurality of terminals 43, wirings 44, a base material 45, and external terminals 46. The plurality of terminals 43 are connected to the connector substrate 10. The wiring 44 is connected to each of the terminals 43. The wirings 44 are covered with the base material 45. The external terminal 46 is connected to a side of the wiring 44 which is opposite to the terminal 43, and is connected to the signal transmission unit 42.

The terminals 43 correspond to the external output terminals 14 of the connector substrate 10 on a one-to-one basis. It is desirable that the number of terminals 43 is the same as the number of external output terminals 14. In FIG. 4, the number of external output terminals 14 is 16. The terminal 43 may have conductivity, and can be formed using a material which is the same as those of the external input terminal 12 and the external output terminal 14.

The wiring 44 transmits information from the terminal 43 to the signal transmission unit 42 through the external terminal 46. The wirings 44 are required to be electrically separated from each other. In order to also avoid a short circuit of the wiring 44, it is preferable that the wirings 44 do not intersect each other when seen in a plan view.

The base material 45 can electrically separate the wirings 44 from each other. In addition, it is preferable that the base material has flexibility, and the base material can be formed using a material which is the same as that of the base material 11 of the connector substrate 10. The wirings 44 may be disposed inside or outside the substrate 45.

The signal transmission unit 42 may be a wired communication device or a wireless communication device as long as the signal transmission unit can transmit a signal to the outside. It is preferable that the signal transmission unit is a wireless communication device from the viewpoint of reducing a sense of incongruity during wearing. For example, communication standards such as Bluetooth (registered trademark), Zigbee (registered trademark), and Wi-Fi (registered trademark) can be used. The signal transmission unit 42 may be mounted with a microcomputer for processing, a lithium battery, or the like.

Figure 5:
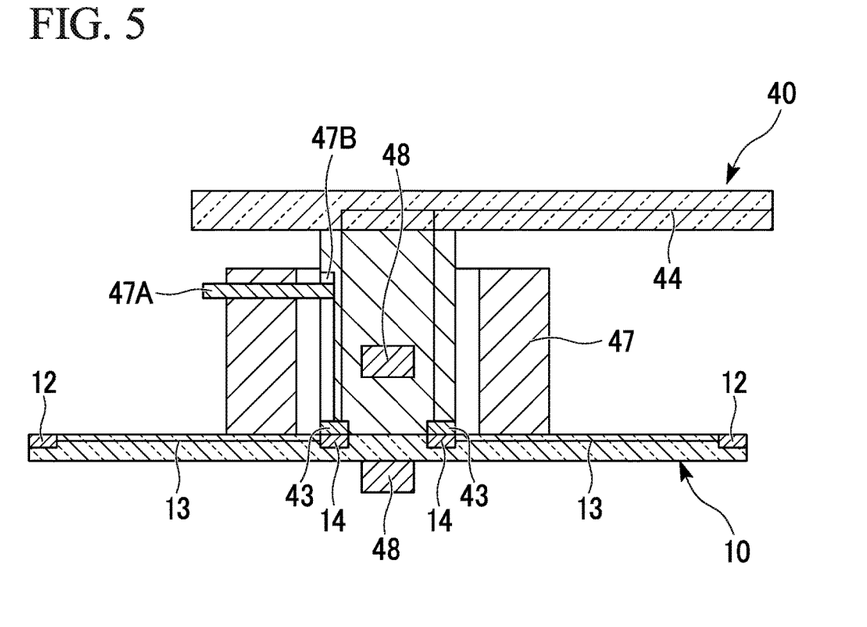
FIG. 5 is a schematic cross-sectional diagram showing a connection portion between the connector substrate and the external output means.

Subsequently, connection of the connector substrate 10 and the external output means 40 will be described. FIG. 5 is a schematic cross-sectional diagram showing a connection portion between the connector substrate and the external output means. As described above, the external output terminals 14 of the connector substrate 10 and the terminals 43 of the external output means 40 are connected to each other on a one-to-one basis.

Each of the connector substrate 10 and the external output means 40 has a fitting portion, and it is preferable that the external output terminals 14 and the terminals 43 are connected to each other through the fitting portions. For example, any one of the connector substrate 10 and the external output means 40 is processed to have a concave shape, and the other one is processed to have a convex shape. The connector substrate 10 and the external output means 40 are processed in this manner, and thus a portion processed to have a convex shape is fitted to a portion processed to have a concave shape. In this manner, it is possible to prevent contact points of the external output terminal 14 and the terminal 43 from being shifted by providing the fitting portions.

In addition, as shown in FIG. 5, a guide member 47 having an opening may be provided between the connector substrate 10 and the external output means 40. The guide member 47 is provided, and thus it is not necessary to process both the connector substrate 10 and the external output means 40. When a convex portion processed to have a convex shape is provided in any one of the connector substrate 10 and the external output means 40, the convex portion can be fitted to the opening of the guide member 47. It is preferable that the convex portion is provided on the external output means 40 side where the terminal 43 is formed. This is because the number of wirings is smaller in the vicinity of the terminal 43 than in the vicinity of the external output terminal 14.

It is preferable that a reference point for determining a position in the circumferential direction thereof is provided in the guide member 47. Since the external output terminals 14 and the terminals 43 correspond to each other on a one-to-one basis, connection of different terminals makes signal processing means process an erroneous signal. The reference point is provided, and thus it is possible to prevent a correspondence relationship between the external output terminals 14 and the terminals 43 from being shifted. As the reference point, for example, a protrusion portion 47A provided in the guide member 47, and the like can be used as shown in FIG. 5. The protrusion portion 47A is matched to a cut portion 47B provided in the convex portion to be fitted to the opening of the guide member 47, and thus it is possible to match positional relationships between the external output terminals 14 and the terminals 43.

The reference point is not limited to a case where the guide member 47 is provided, and it is preferable to provide the reference point also in a case where a convex portion is formed in any one of the connector substrate 10 and the external output means 40 and a concave portion is formed in the other one.

In addition, it is preferable that the connector substrate 10 and the external output means 40 are connected to each other by a magnet 48. The connection of thereof is performed by the magnet 48, and thus it is possible to further facilitate attachment and detachment. The magnet 48 can be formed on a surface opposite to a surface connected to the external output means 40 of the connector substrate 10 and can be formed inside the external output means 40, for example, as shown in FIG. 5. Alternatively, the terminal 43 can also be formed of a conductive magnet.

<Sensor>

The sensor 20 is appropriately provided at a location desired to be measured, as shown in FIG. 1. For this reason, the sensors are not required to be regularly arranged with respect to the connector substrate 10, and may be irregularly disposed with respect to the connector substrate 10.

The type of sensor 20 does not particularly matter. For example, a photodiode, a temperature sensor, a distortion sensor, a pressure sensor, or the like can be used. In addition, a sensor different for each location may be used.

The sensor is not particularly limited as long as a current or a voltage of the sensor changes in association with a change in a physical quantity. However, from convenience of a circuit, but it is preferable to use a variable resistor type sensor in which a resistance changes depending on a physical quantity and voltages at both ends thereof change. As the physical quantity, at least one selected from a group consisting of sound, light, temperature, pressure, and distortion can be used. In this case, it is preferable that a resistance value of the resistance of the sensor is equal to or greater than 50 times that of a wiring resistance of the wiring 30 which is to be described later. Although distance between the connector substrate 10 and the sensor 20 varies depending on a location, the resistance of the sensor is set to be 50 times the wiring resistance, and thus it is possible to exclude the influence of the wiring resistance of the wiring 30.

It is preferable to use a sensor using aqueous ink for the sensor 20. The sensor using aqueous ink is ink obtained by mixing conductive particles with a water dispersion of elastomer. Printing using the ink and drying are performed, and thus conductive particles being randomly dispersed in an elastomer film are obtained. In the sensor, a distance between the conductive particles changes due to pulling, compression, or thermal expansion and contraction due to a change in temperature, and thus resistance at both ends of the sensor changes. The sensor using aqueous ink has an extremely small thickness and has high followability with respect to an object to be measured. For this reason, it is possible to perform accurate and stable measurement.

<Wiring>

The wiring 30 is a conductor that connects each sensor 20 and the connector substrate 10 to each other. Considering processing such as washing or the influence of a wearer's sweat or the like, it is preferable that the vicinity of the wiring 30 is coated with an insulator.

The wiring 30 is constituted by conductive yarns, and it is preferable that the wiring is woven into the fabric body 50. The wiring 30 is woven into the fabric body 50, and thus the wiring 30 can follow the movement of the fabric body 50.

It is preferable that the wiring 30 is disposed on a side opposite to a surface contacting a human body or the like. The disposition of the wiring 30 having conductivity in a portion contacting the human body or the like results in an increase in a concern that a short circuit occurs due to sweat or the like. For this reason, it is preferable that the wiring 30 is disposed at a position separated from the portion contacting the human body or the like.

As the conductive yarn used for the wiring 30, it is possible to use a metal material such as iron or stainless steel, or a material obtained by coating the surface of a general yarn with gold, silver, copper, nickel, copper sulfide, or the like. Among these, the yarn coated with gold, silver, or copper has a small electrical resistance, has safety against a living body, and has strength and twist being freely selectable, and thus is preferable because of a relatively small variation in electric resistance even in a case where the fabric body 50 is washed, and high productivity of a sewing machine or the like.

Regarding the wirings 30, as shown in FIG. 1, it is preferable that the wirings 30 do not intersect each other when seen in a plan view until reaching the connector substrate 10 from the sensors 20. Here, the phrase "do not intersect each other when seen in a plan view" means that the wirings 30 do not intersect each other when seen from the outer surface side where the sensor system is formed.

The wirings 30 connect the sensors 20 and the connector substrate 10 to each other, and thus are disposed in a wide range and are required to have followability with respect to an action. For this reason, the material, thickness, and the like of the insulator with which the wiring 30 can be coated are limited. A sufficient insulating property may not be obtained with such an insulator, and thus there is a concern that a short circuit occurs in a portion where the wirings 30 intersect each other. Particularly, in a case where the wearer sweats or when processing such as washing is performed, a concern for a short circuit increases prominently.

On the other hand, it is possible to use polyimide or the like having a high insulating property for the base material 11 used for the connector substrate 10, as described. For this reason, even when the wiring patterns 13 of the connector substrate 10 intersect each other when seen in a plan view, a short circuit does not occur.

That is, the wirings 30 do not intersect each other when seen in a plan view until reaching the connector substrate 10 from the sensors 20, and thus it is possible to prevent the plurality of wirings 30 from being short-circuited.

<Signal Processing Means>

The signal processing means processes a signal which is output to the outside by the external output means 50. Specifically, potentials of the corresponding first output terminal 14A and second output terminal 14B of the connector substrate 10 are measured, and actions of the sensors 20 are detected from results of the measurement. Biological information such as a motion, electrocardiogram, myoelectricity, and respiration of the body are obtained from information regarding the obtained actions of the plurality of sensors 20.

As the signal processing means, known signal processing means can be adopted. Among the signal processing means, signal processing means that performs machine learning when performing conversion into biological information is preferable. The phrase "machine learning" means that learning for associating the state of a specific living body with the value of the sensor 20 at that time is performed, and the value of the sensor 20 is reversely converted into biological information from a result of the learning. For example, the sensor 20 in a human's arm, leg, or trunk is deformed by the human's motion, which results in a change in a signal. Only in a case of the arm, a signal generated in the sensor 20 is different for each action such as bending, stretching, or torsion. In other words, it can be said that a signal generated in a specific portion by a specific action also includes pieces of information regarding the portion having the signal generated therein and the action. Consequently, whenever the pieces of information are processed, a computer is caused to learn the information, so that the computer itself can more appropriately process a signal when the same action occurs in the same portion. That is, the signal processing means performs machine learning, and thus it is possible to rapidly obtain more pieces of information at the same time.

The connector substrate 10 according to the aspect of the invention is used, and thus it is possible to virtually perform matrix conversion of signals from the sensors 20 provided in various portions of a human body or the like. As a result, even when the sensors 20 are irregularly disposed, signals can be integrated into the connector substrate 10.

In addition, matrix conversion of signals is performed in the connector substrate 10, and thus it is possible to reduce the number of terminals of the external output terminal 14 with respect to the number of terminals of the external input terminal 12 within the connector substrate 10.

When the number of external output terminals 14 can be reduced, for example, the following advantageous effects are produced. For example, when the number of external output terminals 14 is reduced, the size of the connector substrate 10 is reduced. When the size of the connector substrate 10 is small, it is possible to reduce a sense of incongruity during the wearing of the sensor system 100. In addition, connection of the connector substrate 10 and the external output means 40 is facilitated.

In addition, even when an external force is applied due to the connector substrate 10 due to washing or the like, it is possible to reduce an area to be deformed, in a case where the size of the connector substrate 10 is small. As a result, it is possible to avoid a concern for damage or the like due to an external force. When the connector substrate 10 is flexible, the effects become more prominent.

The sensor system 100 according to the aspect of the invention includes the above-described connector substrate 10, and thus the degree of sense of incongruity during wearing is low. In addition, it is easy to attach and detach the external output means 40, and thus it is possible to easily perform processing such as washing. In particular, the wirings 30 are prevented from intersecting each other in portions other than the wiring pattern 13, and thus it is possible to avoid a short circuit and the like in an operation, such as washing, to which moisture is added.

REFERENCE SIGNS LIST

10: CONNECTOR SUBSTRATE
11: BASE MATERIAL
12: EXTERNAL INPUT TERMINAL
12A: FIRST INPUT TERMINAL
12B: SECOND INPUT TERMINAL
13: WIRING PATTERN
13A: FIRST WIRING PATTERN
13B: SECOND WIRING PATTERN
14: EXTERNAL OUTPUT TERMINAL
14A: FIRST OUTPUT TERMINAL
14B: SECOND OUTPUT TERMINAL
14Aa to 14Ah: TERMINAL
14Ba to 14Bh: TERMINAL
20: SENSOR
30: WIRING
40: EXTERNAL OUTPUT MEANS
41: CONNECTOR PORTION
42: SIGNAL TRANSMISSION UNIT
43: TERMINAL
44: WIRING
45: BASE MATERIAL
46: EXTERNAL TERMINAL
47: GUIDE MEMBER
50: FABRIC BODY

What is claimed is:

1. A connector substrate comprising:
a base material;
n first input terminals of m groups which are provided on the base material, m and n being integers equal to or greater than two;
n first output terminals which are provided on the base material;
first wiring patterns which are disposed on or inside the base material and connect the first input terminals and the first output terminals;
m second input terminals which are provided on the base material;
m second output terminals which are provided on the base material; and
second wiring patterns which are disposed on or inside the base material and connect the second input terminals and the second output terminals,
wherein a first end of a first connector wiring constituting one of the first wiring patterns is connected to one of the first input terminals constituting each group, and a second end of the first connector wiring is connected to one of the first output terminals,
the first connector wiring extends from the one of the first input terminals of the each group, and a plurality of first connector wirings constituting the first wiring patterns being disposed to be integrated as one piece extending from the first input terminals to the first output terminals, and
second connector wirings constituting the second wiring patterns are not connected to the first connector wirings constituting the first wiring patterns and third connector wirings constituting a part of the second wiring pattern.

2. The connector substrate according to claim 1, wherein the base material is flexible.

3. The connector substrate according to claim 1, wherein
the first input terminals and the second input terminals are provided in an outer peripheral portion of the base material,
the first output terminals and the second output terminals are provided in a center portion of the base material, and
the first wiring patterns and the second wiring patterns are present at different positions in a thickness direction of the base material inside the base material or on an outer surface of the base material.

4. A sensor system comprising:
the connector substrate according to claim 1;
a plurality of sensors which are classified into the m groups;
a first wiring which connects each of the plurality of sensors and the first input terminals of the connector substrate to each other;
a second wiring which connects two or more sensors of the plurality of sensors to each other, the two or more sensors constituting a group and the second wiring being connected to the second input terminals of the connector substrate;
external output circuit connected to the connector substrate, for outputting a signal;
a signal processor circuit which is configured to process the signal which is output by the external output circuit.

5. The sensor system according to claim 4, wherein the plurality of sensors are irregularly disposed.

6. The sensor system according to claim 4, wherein the first wiring and the second wiring do not intersect each other in a plan view from each of the plurality of sensors until reaching the connector substrate.

7. The sensor system according to claim 4, wherein the connector substrate and the external output circuit are connected to each other by a magnet.

8. The sensor system according to claim 4, wherein the signal processor circuit performs machine learning.

9. The sensor system according to claim 4, wherein the plurality of sensors cause a change in resistance due to a change in at least one physical quantity selected from a group consisting of sound, light, temperature, pressure, and distortion.

10. A wearable sensor system comprising:
a fabric body to which the plurality of sensors and the connector substrate in the sensor system according to claim 4 are attached, wherein the first wiring and the second wiring are provided integrally with the fabric body.

* * * * *